United States Patent [19]
Koibuchi et al.

[11] Patent Number: 4,698,291
[45] Date of Patent: Oct. 6, 1987

[54] PHOTOSENSITIVE COMPOSITION WITH 4-AZIDO-2'-METHOXYCHALCONE

[75] Inventors: Shigeru Koibuchi; Asao Isobe, both of Hitachi; Daisuke Makino, Mito, all of Japan

[73] Assignees: Hitachi Chemical Co., Ltd.; Hitachi, Ltd., both of Tokyo, Japan

[21] Appl. No.: 886,353

[22] Filed: Jul. 17, 1986

Related U.S. Application Data

[63] Continuation of Ser. No. 601,321, Apr. 17, 1984, abandoned.

[30] Foreign Application Priority Data

Apr. 20, 1983 [JP] Japan ................................ 58-69450
Apr. 21, 1983 [JP] Japan ................................ 58-10726

[51] Int. Cl.$^4$ .......................... G03C 1/52; G03C 1/60; G03C 1/72
[52] U.S. Cl. .................................... 430/196; 260/349; 430/197
[58] Field of Search ................ 430/197, 196; 260/349

[56] References Cited

U.S. PATENT DOCUMENTS 3,595,656  7/1971  Ruckert et al. ...................... 430/197
3,869,292  3/1975  Peters ................................. 430/199
3,923,522  12/1975  Hata et al. .......................... 430/197

FOREIGN PATENT DOCUMENTS 53-34902  9/1978  Japan.

Primary Examiner—Charles L. Bowers, Jr.
Attorney, Agent, or Firm—Antonelli, Terry & Wands

[57] ABSTRACT

4'-Azidobenzal-2-methoxyacetophenone is an excellent photosensitive compound and can give a photosensitive composition together with an alkaline-aqueous-solution-soluble polymer which can be insolubilized in an alkaline aqueous solution by photochemical curing with 4'-azidobenzal-2-methoxyacetophenone, and if necessary together with an organic solvent, said composition showing a very small change in viscosity with the lapse of long time.

7 Claims, 5 Drawing Figures

PHOTOSENSITIVE COMPOSITION WITH 4-AZIDO-2'-METHOXYCHALCONE

This is a continuation of application Ser. No. 601,321, filed Apr. 17, 1984 abandoned.

BACKGROUND OF THE INVENTION

The present invention relates to 4'-azidobenzal-2-methoxyacetophenone (i.e., 4-azido-2'-methoxychalcone), a process for producing the same, and a photosensitive composition containing the same for use in the photographic industry, printing industry, electronic industry, etc.

It is known that azide compounds can be used as photosensitive materials and also that polymers soluble in alkaline solution can be used as a film-forming, polymer. These are disclosed in Japanese Patent Appln. Kokoku (Post-Exam Publn) Nos. 22082/70, 26048/69, 34902/78, and 4481/74. When applying photosensitive compositions to various purposes in photographic, printing, electronic, and other industries, it is desirable that azide compounds for use in the compositions be highly soluble in a solvent to be used. Various techniques are adopted for attaining higher solubilities of azide compounds in solvents. For instance, a photosensitive composition comprising 4'-azidobenzal-4-methoxyacetophenone and an alkali-soluble polymer is disclosed in the above Japanese Patent Appln Kokoku (Post-Exam Publn) No. 34902/78. However, 4'-azidobenzal-4-methoxyacetophenone cannot be regarded as having sufficient solubility in solvents probably due to the presence of the methoxy group as a substituent at the 4-position.

On the other hand, there are strict requirements on quality for photosensitive compositions in the field of precision instruments such as electronics. For instance, it is necessary to solve a problem caused by a viscosity change of a composition with the lapse of time since the viscosity change may cause trouble in the process for producing semiconductors or the like.

SUMMARY OF THE INVENTION

An object of this invention is to provide an azide compound which has excellent solubility in a solvent as a negative type of photosensitive compound and can form, in combination with a photosensitive polymer, a composition which exhibits a very small viscosity change with the lapse of time and a process for producing the azide compound.

Another object of the invention is to provide a photosensitive composition comprising a photosensitve compound exhibiting highly improved solubility for a solvent and a polymer which is soluble in an aqueous alkaline solution but can be insolubilized in an alkaline aqueous solution by photochemical curing with the photosensitive compound, said photosensitive composition being particularly improved in showing little viscosity change with the lapse of time.

This invention provides 4'-azidobenzal-2-methoxyacetophenone, which is represented by the formula:

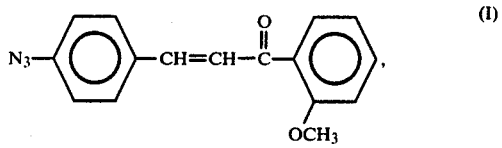

and a process for producing the same.

Further, this invention also provides a photosensitive composition comprising (a) 4'-azidobenzal-2-methoxyacetophenone represented by the formula:

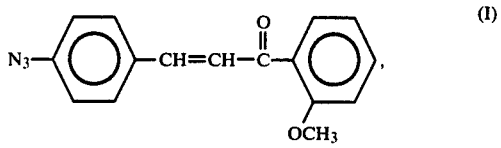

aqueous-solution-soluble polymer which can be insolubilized in an alkaline aqueous solution by photochemical curing with the component (a).

DESCRIPTION OF THE PREFERRED EMBODIMENTS

Figure 1:
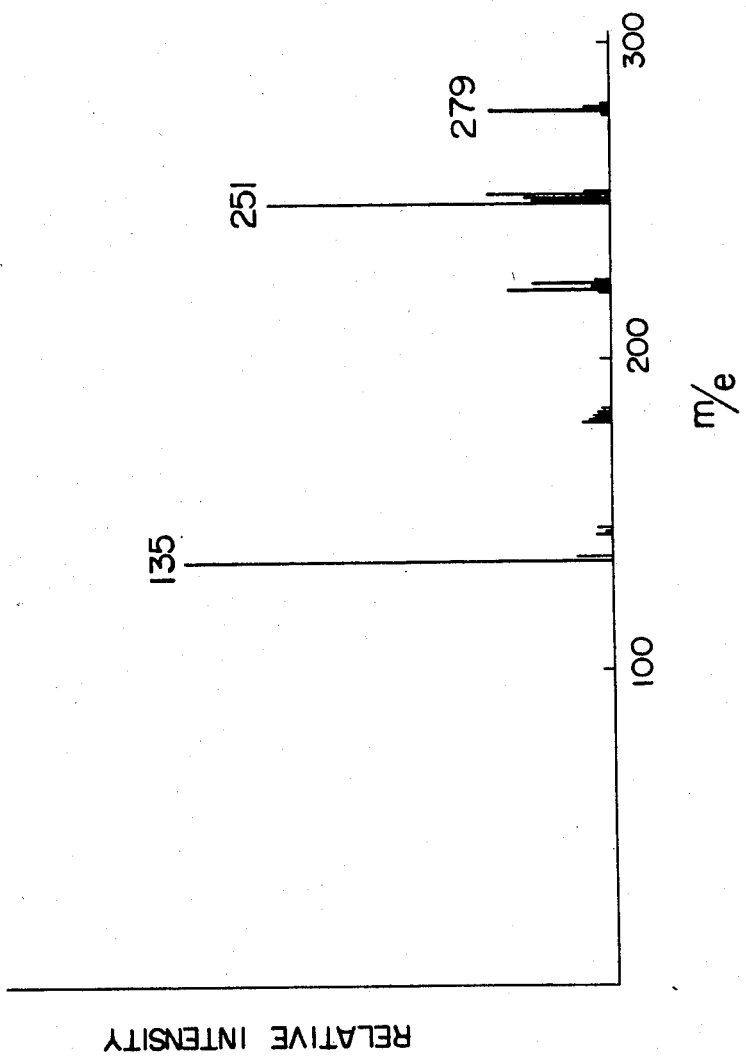
FIG. 1 shows the molecular ion peaks in a mass spectrum of the azide compound of this invention.

4'-Azidobenzal-2-methoxyacetophenone can be synthesized by reacting p-azidobenzaldehyde with 2-methoxyacetophenone in the presence of an alkaline compound as a catalyst. Preferably these reactants are used in nearly equimolar amounts. Suitable alkaline compounds for the catalyst include hydroxides of alkali metals, e.g. sodium hydroxide, potassium hydroxide, etc.

The above reaction is effected in a solvent which can dissolve the alkaline compound. Examples of the solvent are water and alcohols such as methanol and ethanol. The reaction temperature, though not particularly restricted, is preferred to be in the range of 0° to 40° C. from the viewpoint of stability of the product and the reaction rate.

In addition, this synthesis is preferably carried out in yellow light since 4'-azidobenzal-2-methoxyacetophenone of the formula (I) is a photosensitive compound.

4'-Azidobenzal-2-methoxyacetophenone thus obtained can be used for preparing a photosensitive composition together with an alkaline-aqueous-solution-soluble polymer which can be insolubilized in an alkaline aqueous solution by photochemical curing with this azide compound, a solvent, and the like additives.

The alkaline-aqueous-solution-soluble polymer means a high polymer having hydroxyl groups and/or carboxyl groups. Examples thereof are novolak resins, polyhydroxystyrene resins, acrylic and methacrylic polymers. These can be used in the form of homo- or co-condensate or homopolymer or copolymer. Moreover, these can be used alone or as a mixture thereof.

These resins are also available commercially. For example, the novolak resins include a phenol novolak resin, a cresol novolak resin, and a phenol-cresol novolak resin, etc.; the polyhydroxystyrene resins include poly(p-vinylphenol) and a brominated poly(p-vinylphenol), etc.; and acrylic or methacrylic polymers include a homopolymer of acrylic acid or methacrylic acid, copolymers of acrylic acid or methacrylic acid with an acrylic ester or methacrylic ester, and copolymers of acrylic acid or methacrylic acid with styrene.

The alkaline-aqueous-solution-soluble polymer should be capable of forming a film after removal of the solvent and therefore should have a number average molecular weight of preferably at least 500, and more preferably 1000 or more in consideration of heat resistance of the resulting photosensitive composition.

This alkaline-aqueous-solution-soluble polymer is insolubilized in an alkaline aqueous solution by photochemical curing, which can be carried out according to a conventional method by use of a mercury lamp or the like light source. By this curing, the polymer which is soluble in an alkaline aqueous solution becomes insoluble therein and hence developable therewith.

The development is carried out by using, for example, an aqueous solution of sodium hydroxide, potassium hydroxide, or tetramethylammonium hydroxide in a concentration of up to 5% by weight.

The photosensitive composition of this invention may further contain an organic solvent. The photosensitive composition can be coated on a surface of substrate made of, for example, silicon, aluminum, or the like in the form of solution dissolved in an organic solvent. As the organic solvent, there can be used ketones, e.g. acetone, methyl ethyl ketone, methyl isobutyl ketone, cyclohexanone, etc.; Cellosolves, e.g. methyl Cellosolve, methyl Cellosolve acetate, ethyl Cellosolve acetate, etc.,; and esters, e.g. ethyl acetate, butyl acetate, isoamyl acetate, etc. These solvents can be used alone or as a mixture thereof.

A suitable mixing ratio of (a) 4'-azidobenzal-2-methoxyacetophenone to the alkaline-aqueous-solution-soluble polymer is preferably 5:100 to 100:100 by weight, more preferably 10:100 to 50:100 by weight. The content of the organic solvent in the photosensitive composition is preferably 100 to 2000 parts by weight per 100 parts by weight of the components (a) and (b).

When a photosensitive composition comprising a known photosensitive compound, for example, 4'-azidobenzal-3-methoxyacetophenone or 4'-azidobenzal-4-methoxyacetonephenone and the aqueous-alkaline- soluble polymer is allowed to stand in solution form at 20° C., there appears a gradual increase in viscosity after about 3 months and an increase of 10% or more in viscosity after 6 months or more. While the definite allowance for the increase in viscosity is not clear, the smaller the increase of viscosity, the better. The photosensitive composition of this invention shows a distinctly small change in viscosity with the lapse of time as compared with those of the prior art comprising the above-mentioned photosensitive compound and the alkaline-aqueous-solution-soluble polymer.

The photosensitive composition of this invention may further contain one or more conventional auxiliary components depending on purposes of application. Such conventional auxiliary components include, for example, a thermal polymerization inhibitor for the purpose of securing the storage stability a halation inhibitor for the purpose of preventing the halation due to the light reflection from the substrate, an adhesion improver for the purpose of improving the adhesion to the substrate, etc.

This invention is illustrated by way of the following Examples, wherein all parts and percents are by weight unless otherwise specified.

EXAMPLE 1

[Synthesis of 4'-azidobenzal-2-methoxyacetophenone]

In a 500-ml flask were placed 15 g of 2-methoxyacetophenone (made by Aldrich Co., 99% purity), 15 g of p-azidobenzaldehyde (manufactured by Kanto Chemical Co., Ltd.), 50 g of 10% aqueous solution of NaOH, and 50 g of methanol. The mixture was stirred in a yellow light at 25° C. for 24 hours. After completion of the reaction, the deposited crystals were filtered, washed with water, dried, and recrystallized from ethanol.

The 2-methoxyacetophenone used had a purity of 99% and contained almost no isomers different in the position of methoxy substituent. It is sure that the position of methoxy substituent in 2-methoxyacetophenone does not vary during the synthesis in the aqueous alkaline solution.

The thus obtained 4'-azidobenzal-2-methoxyacetophenone was identified by the following analyses:

(A) Mass spectrometry (200° C., 50 eV), m/e=279

FIG. 1 shows an example of the spectrum.

(B) IR spectrometry (KBr method)

Figure 2:
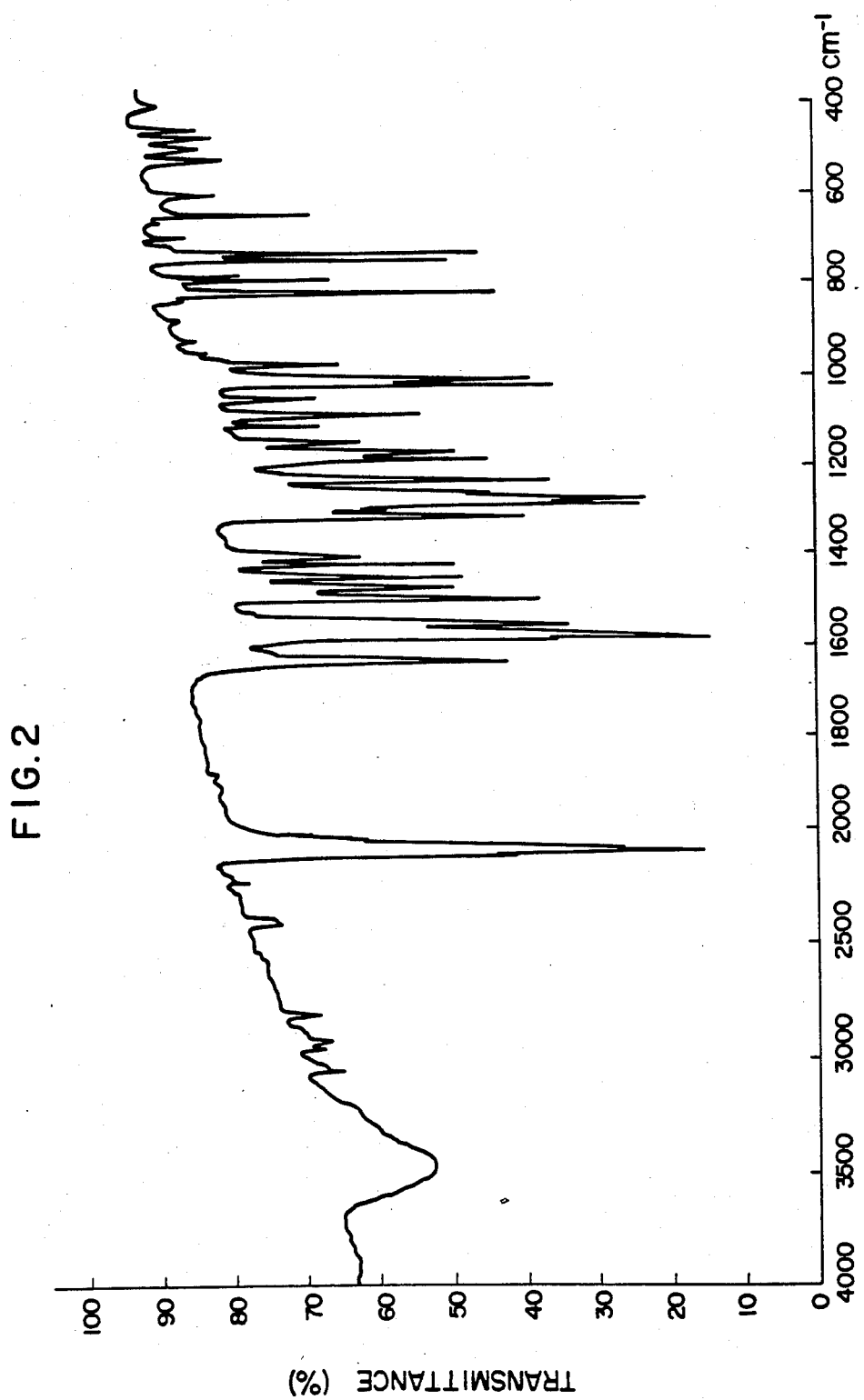
FIGS. 2 and 3 are infrared absorption and NMR spectra, respectively, of the azide compound of this invention.

FIG. 2 shows an example of the spectrum. A strong absorption due to the azido group (—N3) was observed at 2100 cm$^{-1}$.

(C) NMR spectrometry ($^1$H-NMR)

Figure 3:
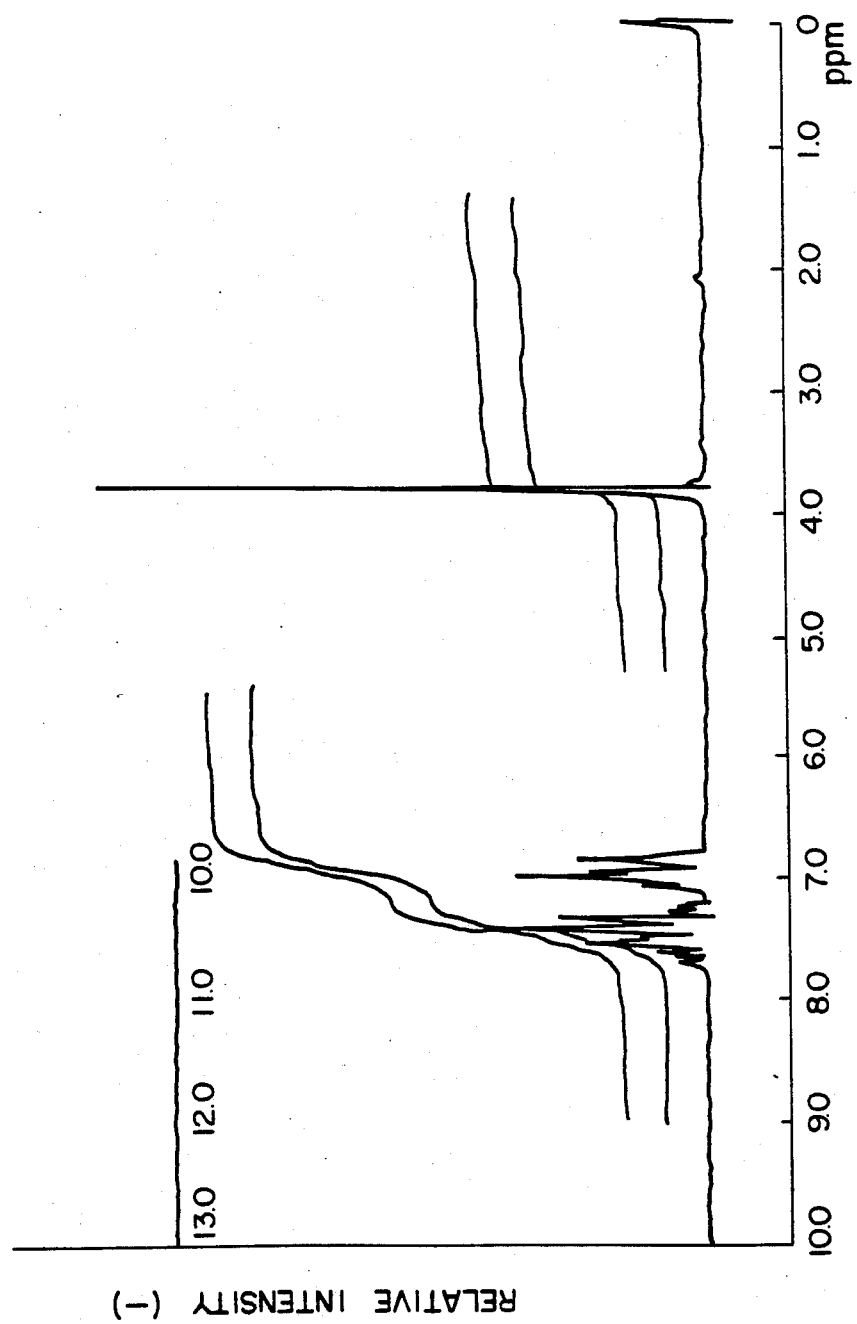

FIG. 3 shows an example of the spectrum. In addition, spectra of the 3-methoxy and 4-methoxy isomers are shown in FIGS. 4 and 5, respectively.

From FIG. 3, —OCH$_3$ and

Figure 4:
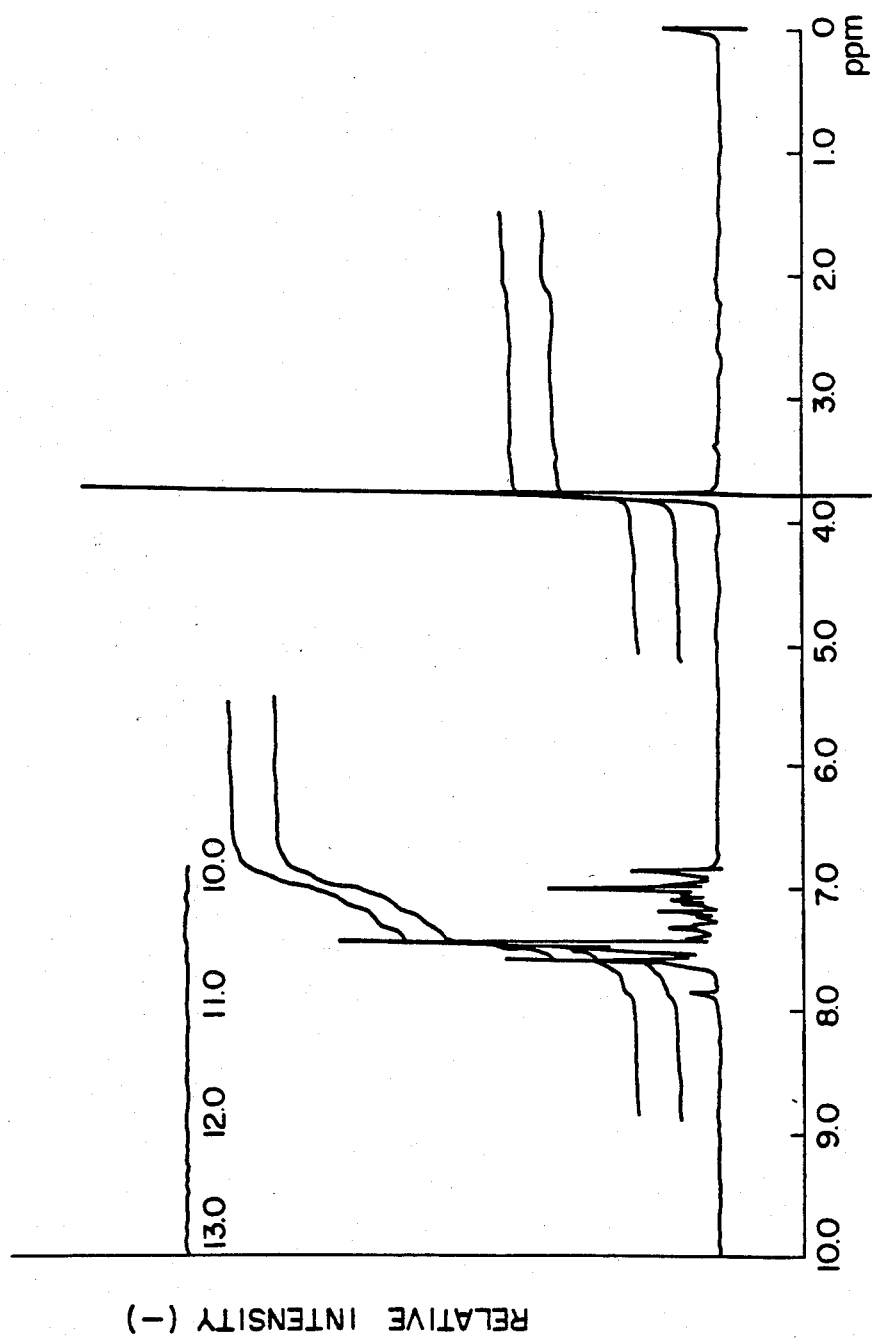
FIGS. 4 and 5 are respective NMR spectra of two analogous compounds.
Figure 5:
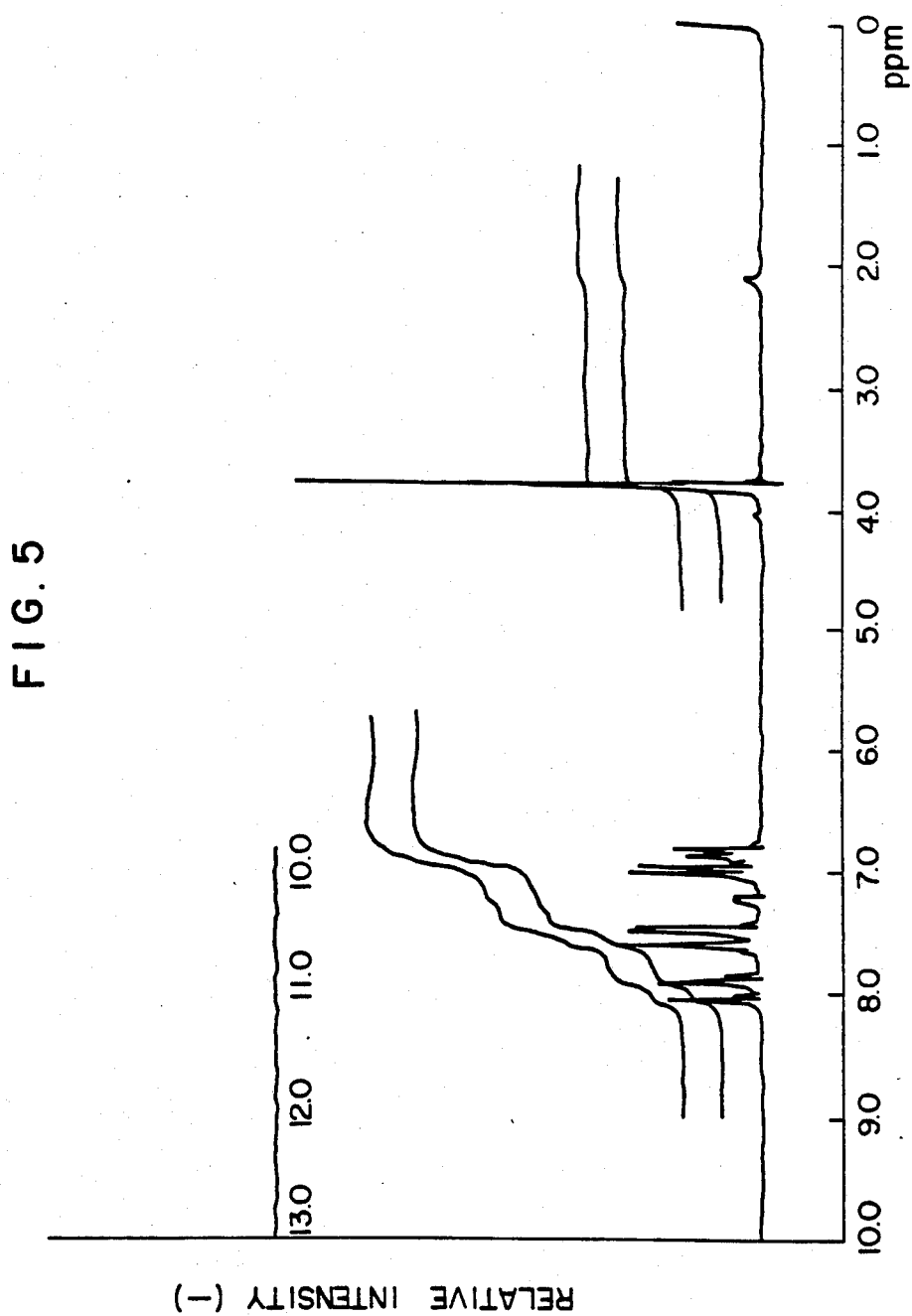

were identified: that is, the presence of 2-methoxy group was confirmed by comparing FIG. 3 with FIGS. 4 and 5, which show comparative examples. The spectrum between 6.8 ppm and 8.1 ppm differs depending upon the position of methoxy substituent (D) Crystal color: Yellow (E) Maximum absorption in ultraviolet absorption spectrum: 330 nm (in ethanol)

(F) Melting point: 90° C.

Solubility at 15° C. of the 4'-azidobenzal-2-methoxyacetophenone synthesized in Example 1 was compared with those of the isomers. The results are as shown in Table 1.

TABLE 1

| Photosensitive compound | Solubility at 15° C. in | | |
|---|---|---|---|
| | Cyclo-hexanone | Ethyl Cellosolve acetate | Isoamyl acetate |
| 4'-Azidobenzal-2-methoxyacetophenone | 3 | 2.8 | 2.8 |
| 4'-Azidobenzal-4-methoxyacetophenone | 1 | 1 | 1 |
| 4'-Azidobenzal-3-methoxyacetophenone | 0.5 | 0.04 | 0.3 |

The solubilities shown in Table 1 are relative values when that of 4-azidobenzal-4-methoxyacetophenone is defined as 1.

EXAMPLE 2

A photosensitive composition was prepared by dissolving 1 part of 4'-azidobenzal-2-methoxyacetophenone synthesized in Example 1 and 5 parts of poly(p-vinylphenol) (manufactured by Maruzen Oil Co., Ltd.) in 25 parts of cyclohexanone. The composition was spin coated at 3000 rpm on an aluminum plate for 30 seconds, and was dried to form a photosensitive coating about 1 μm thick.

The thus coated substrate was exposed to light at an intensity of 10 mW/cm$^2$ (measured on the ray of 365 nm in wavelength) for 10 seconds by using a 250 W mercury lamp. The exposed coating was immersed in a 1% aqueous tetramethylammonium hydroxide solution at 20° C. for 5 minutes, but the coating was not dissolved. When not exposed to the light, the same photosensitive coating was dissolved in 1-2 seconds in the above-mentioned developing solution. Thus, the above obtained composition was proved to be useful as a photosensitive composition.

EXAMPLE 3

A photosensitive compositon was prepared by dissolving 1 part of 4'-azidobenzal-2-methoxyacetophenone prepared in Example 1 and 4 parts of a cresol novolak resin (PSF-2807 a tradename manufactured by Gun-ei Kagaku K.K.) in 25 parts of ethyl Cellosolve acetate. The composition was spin coated on a silicon wafer at 3000 rpm for 30 seconds and was dried to form a photosensitive coating about 1 μm thick.

The photosensitive coating was exposed to light through a chrome mask for 3 seconds by using the same mercury lamp as used in Example 2. Then the coating was treated with a 2% aqueous tetramethylammonium hydroxide solution to dissolve and remove the unexposed portions of the coating, thus forming a pattern of parallel lines with each 2 μm wide and 2 μm of spacing.

EXAMPLE 4

A photosensitive composition was prepared by dissolving 1 part of 4'-azidobenzal-2-methoxyacetophenone synthesized in Example 1 and 4 parts of a 3:7 (molar ratio) methacrylic acid-butyl methacrylate copolymer in 40 parts of methyl Cellosolve acetate.

The composition was spin coated at 3000 rpm on a silicon wafer for 30 seconds, and was dried to form a photosensitive coating about 1.5 μm thick.

The photosensitive coating was exposed to light through a chrome mask for 5 seconds by using the same mercury lamp as used in Example 2. Then the coating was treated with a 2% aqueous tetramethylammonium hydroxide solution to dissolve and remove the unexposed portions of the coating, thus forming a pattern of parallel lines with each 1.5 μm wide and 1.5 μm of spacing.

COMPARATIVE EXAMPLE 1

For comparison, viscosity changes with time were measured on the photosensitive composition of Example 2 and on those prepared by repeating the procedure of Example 2 but using individually two isomers different in methoxy position in place of 4'-azidobenzal-2-methoxyacetophenone. The results were as shown in Table 2.

TABLE 2

| Photosensitive compound | Viscosity change found after 1-month storage at 40° C. |
| --- | --- |
| 4'-Azidobenzal-2-methoxyacetophenone | 5% |
| 4'-Azidobenzal-3-methoxyacetophenone | 15% |
| 4'-Azidobenzal-4-methoxyacetophenone | 10% |

VISCOSITY CHANGE MEASUREMENT CONDITIONS:

Each sample was stored in a container made of a material which can cut rays of 500 nm or less in wavelength, at 40° C. for 1 month. The found viscosity change was compared with that of a sample stored in the same container as the above at 20° C. for 1 month.

As is clear from Tables 1 and 2, 4'-azidobenzal-2-methoxyacetophenone of this invention is more soluble in organic solvents than known azide compounds of the negative type, and gives a photosensitive composition which shows half or less as small a change in viscosity with the lapse of time as do the photosensitive compositions prepared from the known azide compounds.

What is claimed is:

1. A photosensitive composition comprising, in admixture,
(a) 4-azido-2?-methoxychalcone of the formula:

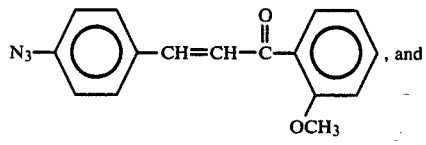

and
(b) an alkaline-aqueous-solution-soluble polymer which can be insolubilized in an alkaline aqueous solution by photochemical curing with the component (a); the proportion of the component (a) being 5 to 100% by weight based on the weight of the component (b);
(c) organic solvent selected from the group consisting of a ketone, a cellusolve and an ester or a mixture thereof, the content of the solvent in the composition being 100 to 2,000 parts by weight per 100 parts by weight of components (a) and (b); said composition exhibiting little viscosity change with a lapse of time when stored as a solution.

2. A composition according to claim 1, wherein the alkaline-aqueous-solution-soluble polymer is a polymer having hydroxyl groups and/or carboxyl groups and having a number average molecular weight of 500 or more.

3. A composition according to claim 2, wherein the alkaline-aqueous-solution-soluble polymer is a novolac resin, a polyhydroxystyrene resin, an acrylic polymer or copolymer, or a methacrylic polymer or copolymer.

4. A composition according to claim 1, wherein the solvent is selected from the group consisting of acetone, methyl ethyl ketone, methyl isobutyl ketone, cyclohexanone, methyl cellosolve, methyl cellosolve acetate, ethyl cellosolve acetate, ethyl acetate, butyl acetate, and isoamyl acetate.

5. A composition according to claim 1, wherein said organic solvent is selected from the group consisting of cyclohexanone, ethyl cellosolve acetate and isoamyl acetate.

6. A composition according to claim 1, wherein the organic solvent is cyclohexanone.

7. A composition according to claim 1, wherein said solution of said composition is formed in a solvent in which the 4-azido-2'-methoxychalcone has excellent solubility.

* * * * *